(12) United States Patent
Koohang et al.

(10) Patent No.: US 10,300,471 B2
(45) Date of Patent: May 28, 2019

(54) RUTHENIUM-CATALYZED SYNTHESIS OF BIARYL COMPOUNDS IN WATER

(71) Applicant: CHICAGO DISCOVERY SOLUTIONS, LLC, Chicago, IL (US)

(72) Inventors: Ali Aiden Koohang, Cornelius, NC (US); Anita Mehta, Darien, IL (US)

(*) Notice: Subject to any disclaimer, the term of this patent is extended or adjusted under 35 U.S.C. 154(b) by 24 days.

(21) Appl. No.: 15/028,276

(22) PCT Filed: Oct. 6, 2014

(86) PCT No.: PCT/US2014/059281
§ 371 (c)(1),
(2) Date: Apr. 8, 2016

(87) PCT Pub. No.: WO2015/054120
PCT Pub. Date: Apr. 16, 2015

(65) Prior Publication Data
US 2016/0263565 A1 Sep. 15, 2016

Related U.S. Application Data

(60) Provisional application No. 61/961,224, filed on Oct. 8, 2013.

(51) Int. Cl.
*C07C 47/11* (2006.01)
*C07D 213/16* (2006.01)
*C07D 215/233* (2006.01)
*C07D 263/38* (2006.01)
*C07D 403/10* (2006.01)
*B01J 31/22* (2006.01)
*C07D 213/24* (2006.01)
*C07D 413/14* (2006.01)
*C07B 37/04* (2006.01)
*C07F 15/00* (2006.01)

(52) U.S. Cl.
CPC ........... *B01J 31/2295* (2013.01); *C07B 37/04* (2013.01); *C07C 47/11* (2013.01); *C07D 213/16* (2013.01); *C07D 213/24* (2013.01); *C07D 215/233* (2013.01); *C07D 263/38* (2013.01); *C07D 403/10* (2013.01); *C07D 413/14* (2013.01); *C07F 15/0046* (2013.01)

(58) Field of Classification Search
None
See application file for complete search history.

(56) References Cited

U.S. PATENT DOCUMENTS

2008/0177114 A1 7/2008 Goossen et al.
2012/0232283 A1 9/2012 Seki

FOREIGN PATENT DOCUMENTS

WO WO 2005/037756 A2 4/2005
WO WO 2011/131027 A1 * 10/2011

OTHER PUBLICATIONS

Baird, MC. et al. Benzene Complexes of Ruthenium(II). Canadian Journal of Chemistry. 1972, vol. 50, p. 3063.*
Cortez, NA. et al. New C2-symmetric bis(sulfonamide-cyclohexane-1,2-diamine-RhCp* complex and its application in the asymmetric transfer hydrogenation (ATH) of ketones in water. Tetrahedron Letters. 2006, vol. 47, p. 8516.*
Cortez, Norma A., et al., "New C2-symmetric bis-sulfonamide)-cyclohexane-1,2-diamine-RhcP complex and its application in the asymmetric transfer hydrogenation (ATH) of ketones in water," *Tetrahedron Letters* 47(48):8515-8158 (2006).
International Search Report and Written Opinion for related International Application No. PCT/US2014/059281, dated Mar. 17, 2015 (— pages).
PUBCHEM, Compound Summary for CID 59351792, 11 pages (Aug. 20, 2012).
PUBCHEM, Compound Summary for CID 73819, 16 pages (Mar. 27, 2005).

* cited by examiner

*Primary Examiner* — Timothy R Rozof
(74) *Attorney, Agent, or Firm* — Brinks Gilson & Lione; Ryan L. Marshall

(57) ABSTRACT

Using a $[RuCl_2(arene)]_2$ complex and a formate source, a directed ortho C—H insertion and aryl-aryl coupling sequence in water provides biaryl compounds useful in the preparation of biologically active molecules and intermediates. Reactions may be conducted in the ambient atmosphere. Ruthenium catalysts prepared from $[RuCl_2(arene)]_2$ and a formate source may be prepared in situ or isolated for later use.

2 Claims, No Drawings

RUTHENIUM-CATALYZED SYNTHESIS OF BIARYL COMPOUNDS IN WATER

REFERENCE TO EARLIER FILED APPLICATIONS

This application is a 371 national phase of PCT/US2014/059281, filed Oct. 6, 2014, and claims the benefit under 35 U.S.C. § 119(e) of U.S. Provisional Application No. 61/961,224, filed Oct. 8, 2013, the disclosures of which are incorporated, in their entirety, by this reference.

BACKGROUND OF THE INVENTION

1. Field of the Invention

The present invention relates to novel ruthenium catalysts and their use for performing carbon-carbon bond formation in aqueous media to produce useful biaryl compounds.

2. Description of the Related Art

Synthesis of biaryl moieties are of special interest as they are commonly found in many organic compounds including oils, drugs, flavors, petrochemicals, fragrances and food. For example, biphenyl moieties appear in many drug molecules such as losartan, valsartan, azilsartan, and anacetrapib, among others. Biaryls even appear in the liquid crystal mixture of commercial liquid crystal displays (LCD) as cyano-substituted biphenyl molecules containing long aliphatic tails. Biaryl moities are found in intermediate structures during the production of emulsifiers, optical brighteners, crop production products, and plastics. Substituted biphenyl structures are repeatedly found in natural products such as alkaloids and appear in numerous biologically active agents in pharmaceutical and agrochemical specialties. Polyaromatic compounds containing multiple aryl-aryl bonds possess original physical properties, which could lead to applications as organic conductors or semiconductors. Di- or tri-aromatic rings are also the backbone of ligands used for asymmetric catalysis.

Biaryl compounds are commonly prepared using well-known reactions such as the Suzuki and Stille couplings. These processes require one of the reaction partners to have either a boron or tin-bearing carbon, respectively, at the carbon where bond formation takes place. Alternatively, biaryl bonds may be formed using transition metal-catalyzed directed ortho functionalization and coupling. This process employs an aryl reactant bearing a substituent capable of directing transition metal insertion at the ortho position, thereby allowing bond formation between the site of metal insertion and a carbon atom on a reaction partner substituted with a suitable leaving group (e.g., a halide). Ortho DG's (Directing Groups) are strong coordinating or chelating groups that have the effect of increasing the kinetic acidity of protons in the ortho-position.

Typically, transition metal-catalyzed ortho C—H functionalization and coupling are achieved in N-methylpyrrolidinone (NMP), dimethylformamide (DMF), dimethylacetamide (DMAc), or similar solvents. These solvents are undesirable because of their toxicity and/or high boiling points. Also, coupling reactions with transition metals are often carried out under inert atmosphere, such as with a Schlenk tube, due to sensitivity of the catalyst to the ambient atmosphere. Thus, because of disposal and toxicity issues, and general ease in handling and manipulation, there is an interest in finding more environmentally friendly processes for forming biaryl bonds by transition metal-catalyzed ortho C—H functionalization and coupling.

SUMMARY OF THE INVENTION

The present invention relates to novel ortho directing groups, ruthenium catalysts and methods for effecting ortho C—H metalation and coupling in aqueous media to form useful biaryl compounds. In a first aspect of the invention, a first aryl compound is reacted with a second aryl compound in water in the presence of a catalytically effective amount of a $[RuCl_2(arene)]_2$ complex and a source of formate. The first aryl compound includes first and second ring atoms where the second ring atom is appended with a directing group and the first ring atom is located in the ortho position with respect to the second ring atom and is the site of reaction with the second aryl compound. In turn, the second aryl compound includes a first ring atom that is substituted with a leaving group. The reaction between the first aryl compound and the second aryl compound results in the formation of a carbon-carbon bond between the first ring atom of the first aryl compound and the first ring atom of the second aryl compound.

A second aspect of the invention provides ruthenium catalysts prepared by the reaction of a $[RuCl_2(arene)]_2$ complex with a source of formate. The ruthenium catalysts may be prepared in situ or isolated and may be used to prepare useful biaryl compounds.

A third aspect of the invention provides a new ortho directing group of formula

protected derivatives thereof, and methods of use thereof to prepare useful biaryl compounds.

DETAILED DESCRIPTION

1. Definitions

The term "aryl" as used herein, refers to a carbocyclic aryl or a heteroaryl as those terms are defined herein.

The terms "biaryl" or "biaryl compound" as used herein, refer to molecules containing two aryl rings connected by a carbon-carbon single bond. The individual aryl rings may be either carbocyclic aryl or heteroaryl.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched chain hydrocarbon and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, means a straight or branched chain hydrocarbon and containing at least one carbon-carbon triple bond. Representative examples include propynyl, butynyl, pentynyl, and the like.

The term "alkylene," as used herein, means a divalent group derived from a straight or branched chain hydrocarbon. Representative examples of alkylene include, but are not limited to, —$CH_2$—, —$CH_2CH_2$—, —$CH_2CH_2CH_2$—, —$CH_2CH(CH_3)CH_2$—, and —$CH_2CH(CH_3)CH(CH_3)CH_2$—.

The term "alkenylene," as used herein, means a divalent group derived from a straight or branched chain hydrocarbon and containing at least one carbon-carbon double bond. Representative examples of alkenylene include, but are not limited to —CH=CH—, —$CH_2$CH=CH—, and —$CH_2$CH=CH($CH_3$)—.

The term "alkynylene," as used herein, means a divalent group derived from a straight or branched chain hydrocarbon and containing at least one carbon-carbon triple bond. Representative examples of alkynylene include, but are not limited to —$CH_2$—C≡C—, —$CH_2CH_2$—C≡C—, and —C≡C—$CH_2CH(CH_3)CH_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkoxyalkyl" as used herein means an alkoxy group, as defined herein, appended to the parent molecular moiety through an alkylene group of 1 to 4 carbons. Representative examples of alkoxyalkyl include, but are not limited to, methoxymethyl, ethoxymethyl, methoxyethyl, etc.

The term "alkylcarbonyl" as used herein, means an alkyl group, as defined herein, appended to the parent molecular moiety through a C(O) group.

The terms "haloalkyl," "haloalkenyl," and "haloalkynyl" as used herein, mean, respectively an alkyl, alkenyl, or alkynyl group, as defined herein, in which one, two, three, four, five, six, or seven hydrogen atoms are replaced by halogen. For example, representative examples of haloalkyl include, but are not limited to, 2-fluoroethyl, 2,2-difluoroethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein appended to the parent molecular moiety through an alkylene group of 1 to 4 carbons. Representative examples include, but are not limited to, trifluoromethoxymethyl, trifluoromethoxyethyl, etc.

The term "carbocyclic aryl," as used herein, means phenyl or a bicyclic ring system containing an aromatic ring wherein all of the ring members of the bicyclic ring system are carbons. The bicyclic carbocyclic aryl is naphthyl, dihydronaphthalenyl, tetrahydronaphthalenyl, indanyl, or indenyl. The phenyl and bicyclic carbocyclic aryls are attached to the parent molecular moiety through any carbon atom contained within the phenyl or bicyclic carbocyclic aryl.

The term "arene," as used herein, means an optionally substituted aromatic ring system. Representative examples include p-cymene, benzene, naphthalene, mesitylene, toluene, xylene, hexamethylbenzene, indane, biphenyl, etc.

The term "heteroaryl," as used herein, means a monocyclic heteroaryl or a fused bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is an 8- to 12-membered ring system having a monocyclic heteroaryl fused to an additional ring; wherein the additional ring may be aromatic or partially saturated, and may contain additional heteroatoms. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, furopyridinyl, indolyl, indazolyl, isoquinolinyl, naphthyridinyl, oxazolopyridine, quinolinyl, thienopyridinyl, 5,6,7,8-tetrahydroquinolinyl, 6,7-dihydro-5H-cyclopenta[b]pyridinyl, and 2,3-dihydrofuro[3,2-b]pyridinyl. The monocyclic and the bicyclic heteroaryl groups are connected to the parent molecular moiety through any substitutable carbon atom or any substitutable nitrogen atom contained within the groups.

The term "cycloalkyl" as used herein, means a carbocyclic ring system containing 3, 4, 5, 6, 7, or 8 carbon atoms and zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups of the present invention may contain an alkylene bridge of 1, 2, 3, or 4 carbon atoms, linking two non-adjacent carbon atoms of the group. Examples of such bridged systems include, but are not limited to, bicyclo[2.2.1]heptanyl and bicyclo[2.2.2]octanyl. The cycloalkyl groups described herein can be appended to the parent molecular moiety through any substitutable carbon atom.

The term "cycloalkenyl" as used herein, means a carbocyclic ring system containing 5, 6, 7, or 8 carbon atoms and zero heteroatoms as ring atoms, and one or two double bonds. Representative examples include cyclopentenyl, cyclohexenyl, etc.

The terms "arylalkyl," "heteroarylalkyl," "carbocyclic arylalkyl" and the like refer to aryl, heteroaryl, or carbocyclic aryl groups, as defined herein, appended to the parent molecular moiety through an alkylene group of 1 to 4 carbons. Representative examples include benzyl, phenethyl, imidazolylmethyl, indolylmethyl, pyridinylmethyl, etc.

The term "heterocycle," "heterocyclic", or "heterocyclyl" as used herein, refers to a monocyclic heterocycle, a bicyclic heterocycle, or a spirocyclic heterocycle. The monocyclic heterocycle is a 3, 4, 5, 6, 7, or 8-membered ring containing at least one heteroatom selected from O, N, or S. The 3 or 4 membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4- dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The bicyclic heterocycle is a 5-12-membered ring system having a monocyclic heterocycle fused to a phenyl, a saturated or partially saturated carbocyclic ring, or another monocyclic heterocyclic ring. Representative examples of bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle or heterocyclyl means a 4, 5-, 6-, 7-, or 8-membered monocyclic heterocycle ring wherein two of the substituents on the same carbon atom form a 3-, 4-, 5-, or 6-membered monocyclic ring selected from the group consisting of cycloalkyl and heterocycle, each of which is optionally substituted with 1, 2, 3, 4, or 5 alkyl groups. Examples of a spiroheterocycle include, but are not limited to, 1,3-diazaspiro[4.4]non-1-ene, 5-oxaspiro[3,4]octane and 8-azaspiro[4.5]decane. The spirocyclic heterocycle may be substituted such as, for example, with an oxo and/or $C_{1-6}$alkyl (e.g., 2-butyl-1,3-diazaspiro[4.4]non-1-en-4-one). The monocyclic and bicyclic heterocycle groups of the present invention may contain an alkylene bridge of 1, 2, 3, or 4 carbon atoms, linking two non-adjacent atoms of the group. Examples of such a bridged heterocycle include, but are not limited to, 2-azabicyclo[2.2.1]heptanyl, 2-azabicyclo[2.2.2]octanyl, 1,2,3,4-tetrahydro-1,4-methanoisoquinolinyl, and oxabicyclo[2.2.1]heptanyl. The monocyclic, bicyclic, and spirocyclic heterocycle groups are connected to the parent molecular moiety through any substitutable carbon atom or any substitutable nitrogen atom contained within the group.

Terms such as "alkyl," "cycloalkyl," "alkylene," etc. may be preceded by a designation indicating the number of atoms present in the group in a particular instance (e.g., "$C_{1-6}$alkyl," "$C_{3-6}$cycloalkyl," "$C_{2-6}$alkynylene," "$C_{2-6}$alkenylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-6}$," the members of the group that follows may have any number of carbon atoms falling within the recited range. A "$C_{1-6}$alkyl," for example, is an alkyl group having from 1 to 6 carbon atoms, however arranged (i.e., straight chain or branched).

In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule. Representative hydroxyl protecting groups, for example, are disclosed by Beaucage et al. (Tetrahedron 1992, 48, 2223-2311). Further hydroxyl protecting groups, as well as other representative protecting groups, are disclosed in Greene and Wuts, Protective Groups in Organic Synthesis, Chapter 2, 2d ed., John Wiley & Sons, New York, 1991. Examples of hydroxyl protecting groups include, but are not limited to, t-butyl, t-butoxymethyl, methoxymethyl, tetrahydropyranyl, I-ethoxyethyl, 1-(2-chloroethoxy) ethyl, 2-trimethylsilylethyl, p-chlorophenyl, 2,4-dinitrophenyl, benzyl, 2,6-dichlorobenzyl, diphenylmethyl, p,p'dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

2.0 Aryl-Aryl Coupling Processes

The present invention provides processes for forming a biaryl compound in water by an ortho-directed ruthenium C—H insertion aryl-aryl coupling sequence. According to the first aspect of the invention, a first aryl compound is reacted with a second aryl compound in water in the presence of a catalytically effective amount (e.g., about 0.01 to about 0.3 equivalents) of a $[RuCl_2(arene)]_2$ complex and a source of formate. The first aryl compound includes first and second ring atoms, the second ring atom being appended with a directing group and where the first ring atom is located in the ortho position with respect to the second ring atom and is the site of reaction with the second aryl compound. In turn, the second aryl compound includes a first ring atom that is substituted with a leaving group. The reaction between the first aryl compound and the second aryl compound results in the formation of a carbon-carbon bond between the first ring atom of the first aryl compound and the first ring atom of the second aryl compound. The overall process may be depicted as shown in equation (1), where $Ar_1$ is the first aryl compound, $Ar_2$ is the second aryl compound, DG is an ortho directing group, and X is a suitable leaving group.

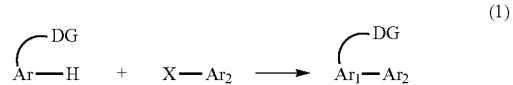

(1)

The DG may be appended to the second ring atom of the first aryl ring by direct attachment, or may be appended to the second ring atom by an intervening linker, or may be attached in either of the preceding manners and also have a second linker from the DG to a third ring atom of the first aryl ring so as to form an additional ring of 5- to 7-members, such as the ring G:

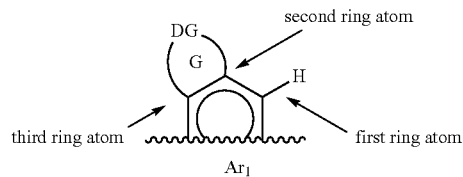

In some embodiments according to the first aspect, the ortho directing group DG is —$COR^{10}$, —$COOR^{10}$—$CONR^7R^8$, —$NR^9COR^{10}$, —$NR^9CO_2R^{10}$, —$OCONR^7R^8$, —O-methoxymethyl (i.e., —OMOM), —$SO_2R^{10}$, —$SOR^{10}$, —$SO_3H$, —CH=$NR^{11}$, —$SO_2NR^7R^8$, —$SONR^7R^8$, —CN, —$SO_2tBu$, —$CF_3$, —NC, —$OR^{10}$, —F, —Cl, Br, I, —S-Ph, —SR$^{10}$, —NR$^7$R$^8$, —OP(O)OR$^{10}$, —CH(OC$_{1-4}$alkyl)$_2$, —CH(OH)(NR$^7$),

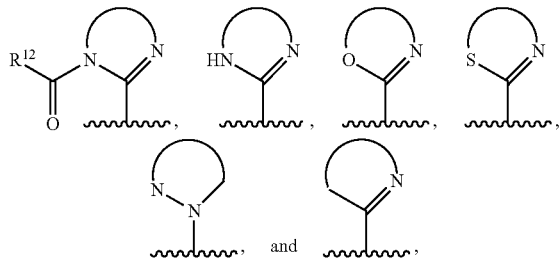

or a salt or protected derivative thereof, and R$^7$, R$^8$, R$^9$, and R$^{12}$ are each independently hydrogen, C$_{1-6}$alkyl, or C$_{1-6}$alkoxy, and R$^{10}$ and R$^{11}$ are each independently hydrogen or C$_{1-6}$alkyl; or R$^7$, R$^8$, R$^9$, R$^{10}$, R$^{11}$, and R$^{12}$ each, independently, form an alkylene or alkenylene linker to a third ring atom of the first aryl ring to form a 5- to 7-membered ring wherein one or more carbon atoms of the alkylene and alkenylene linker is optionally replaced with an oxygen, sulfur, or nitrogen atom.

Representative examples of R$^7$, R$^8$, R$^9$, R$^{10}$, R$^{11}$, and R$^{12}$ forming an alkylene/alkenylene linker to a third ring atom of the first aryl ring include:

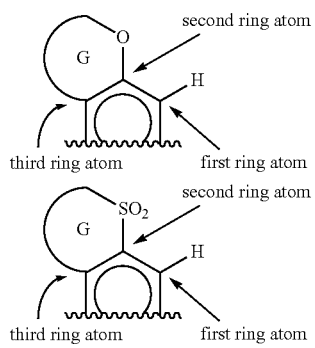

The group

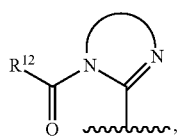

as used herein, includes 5- to 7-membered ring systems and may be further substituted with one or more groups including, but not limited to, C$_{1-4}$alkyl, C$_{1-4}$haloalkyl, and C$_{1-4}$alkoxy. In some embodiments,

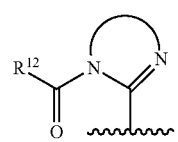

is a partially unsaturated heterocycle substituted with C(O)R$^{12}$. Representative examples include

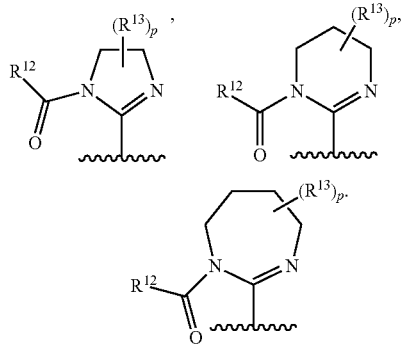

The group

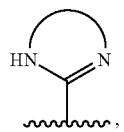

as used herein, includes 5- to 7-membered ring systems and may be further substituted at a ring carbon and/or ring nitrogen with one or more groups including, but not limited to, a protecting group, C$_{1-4}$alkyl, C$_{1-4}$haloalkyl, and C$_{1-4}$alkoxy. Also as used herein,

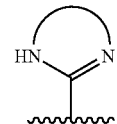

is optionally substituted with an alkylene or alkenylene linker to a third ring atom of the first aryl ring to form a 5- to 7-membered ring wherein one or more carbon atoms of the alkylene and alkenylene is optionally replaced with an oxygen, sulfur, or nitrogen atom. In some embodiments,

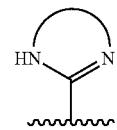

is a partially unsaturated heterocycle. In other embodiments,

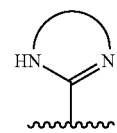

is a 5-membered heteroaryl. Representative examples include

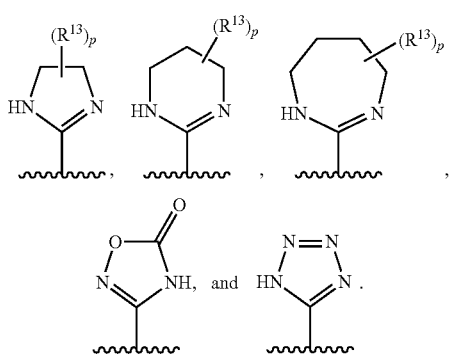

The group

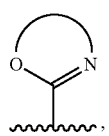

as used herein, includes 5- to 7-membered ring systems and may be further substituted with one or more groups including, but not limited to, a protecting group, $C_{1-4}$alkyl, $C_{1-4}$haloalkyl, and $C_{1-4}$alkoxy. In some embodiments,

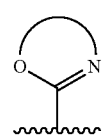

is a partially unsaturated heterocycle. Representative examples include

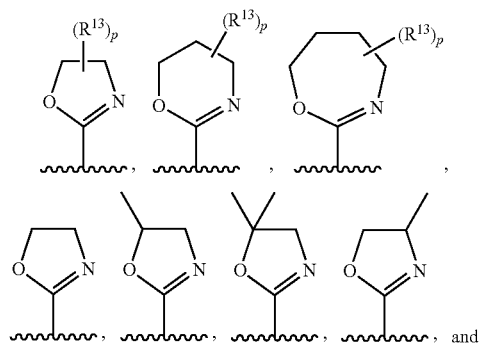

The group

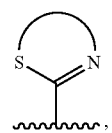

as used herein, includes 5- to 7-membered ring systems and may be further substituted with one or more groups including, but not limited to, a protecting group, $C_{1-4}$alkyl, $C_{1-4}$haloalkyl, and $C_{1-4}$alkoxy. In some embodiments,

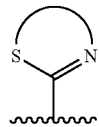

is a partially unsaturated heterocycle. Representative examples include

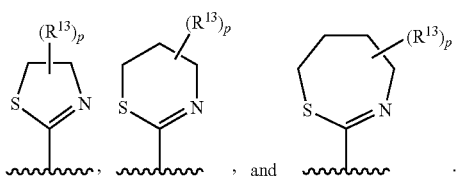

The group

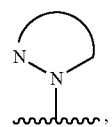

as used herein, includes 5- to 7-membered ring systems and may be further substituted with one or more groups including, but not limited to, a protecting group, $C_{1-4}$alkyl, $C_{1-4}$haloalkyl, and $C_{1-4}$alkoxy. Also as used herein,

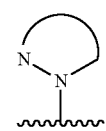 [SMILES: *N(C)N]

is optionally substituted with an alkylene or alkenylene linker to a third ring atom of the first aryl ring to form a 5- to 7-membered ring wherein one or more carbon atoms of the alkylene and alkenylene is optionally replaced with an oxygen, sulfur, or nitrogen atom. In some embodiments,

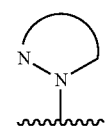

is a 5-membered heteroaryl. Representative examples include

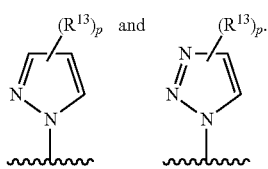

The group

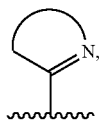

as used herein, includes 5- to 7-membered ring systems and may be further substituted with one or more groups including, but not limited to, a protecting group, $C_{1-4}$alkyl, $C_{1-4}$haloalkyl, and $C_{1-4}$alkoxy. Also as used herein,

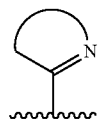

is optionally substituted with an alkylene or alkenylene linker to a third ring atom of the first aryl ring to form a 5- to 7-membered ring wherein one or more carbon atoms of the alkylene and alkenylene is optionally replaced with an oxygen, sulfur, or nitrogen atom. In some embodiments,

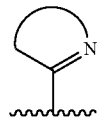

is a 6-membered heteroaryl. Representative examples include

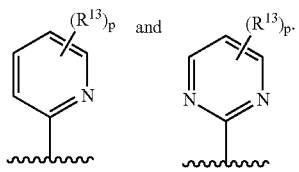

In other embodiments

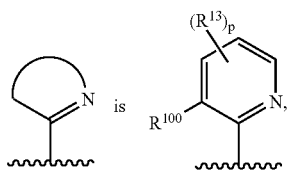

wherein $R^{100}$ is hydrogen or $C_{1-6}$alkyl. In other embodiments $R^{100}$ together with a third atom of the first aryl compound forms a 5- to 7-membered ring. In some embodiments, $R^{100}$ is an unsaturated bridge to the third ring atom of the first aryl compound to form

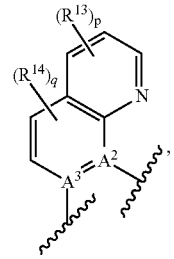

where $A^2$ is the second ring atom of the first aryl compound, $A^3$ is the third ring atom of the first aryl compound, $R^{14}$ is an optional substituent and q is 0, 1, or 2.

In the foregoing embodiments, $R^{13}$ and $R^{14}$ are optional substituents that include but are not limited to halogen, CN, $C_{1-4}$alkyl, $C_{1-4}$haloalkyl, $C_{1-4}$alkoxy, $C_{1-4}$haloalkoxy, $C_{1-4}$alkyl-S—, $C_{1-4}$alkylC(O)—, $C_{3-6}$cycloalkyl, $C_{1-4}$alkyl-O—C(O)—, $C_{1-4}$alkyl-NH—C(O)—, and $(C_{1-4}$alkyl$)_2$N—C(O)—.

In the foregoing embodiments, p may be any integer or range of integers within the range from 0 to 5.

In some embodiments the directing group is selected from the group consisting of:

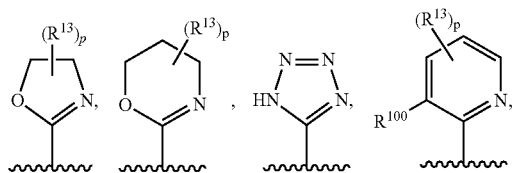

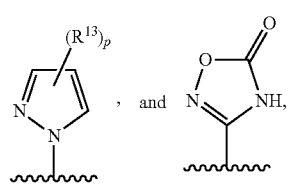

or a salt or protected derivative thereof.

In other embodiments, the directing group is selected from

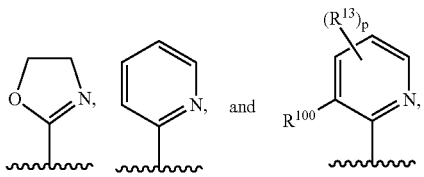

wherein $R^{100}$ together with the second ring atom and third ring atom of the first aryl compound forms

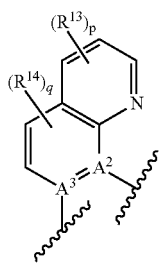

In some embodiments, the directing group DG is directly substituted on the second ring atom of the first aryl compound without an intervening linker. For example, as shown below, an oxazoline DG is directly substituted on the second ring atom of $Ar_1$.

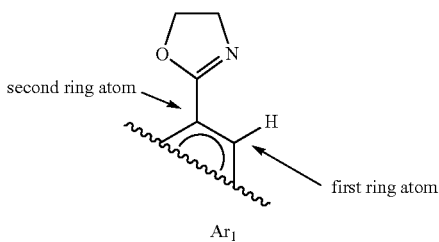

In other embodiments, as shown below, DG is directly substituted on the second ring atom of the first aryl compound with additional ring fusion to the third ring atom, where G represents the additional fused ring and the DG is the embedded pyridine ring:

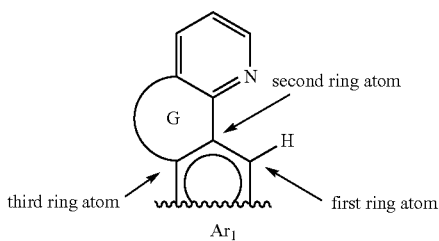

In other embodiments, the directing group is appended to the second ring atom of the first aryl compound by an intervening linker $L^1$, wherein $L^1$ is a chain comprising 1-5 atoms selected from carbon, nitrogen, oxygen, or sulfur or $L^1$ is a ring selected from $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano.

For example, the directing group —$NR^7R^8$ may be appended to the second ring atom by a chain that includes oxygen and carbon atoms such as where $L^1$ is —$OCH_2CH_2$— and $L^1$-DG is —$OCH_2CH_2$—$NR^7R^8$.

In another example, the oxy anion directing group —$O^-$ may be appended to the second ring atom by an alkylene chain, such as where $L^1$ is $CH_2$ and $L^1$-DG is —$CH_2$—$O^-$.

In some embodiments together with the foregoing, the leaving group on the second aryl compound is bromo, chloro, iodo, or other suitable derivative. Preferably, the leaving group is bromo.

In still other embodiments in combination with the foregoing, the formate source is an alkali metal formate (e.g., sodium formate), alkaline earth metal formate (e.g., magnesium formate), $N(R^{20})_4HC(O)O$, $HC(O)$—$OC_{1-6}$ alkyl, NaCHSO (sodium thioformate), sodium formamide, CHO—COOH (glyoxal), sodium glyoxalate or potassium glyoxalates, or a combination thereof; and $R^{20}$ is hydrogen or $C_{1-6}$alkyl. For example, in some embodiments, the formate source is lithium formate, sodium formate, potassium formate, or cesium formate. In some embodiments, the formate source is magnesium formate or calcium formate. In certain preferred embodiments, the formate source is sodium formate. In still other embodiments, the formate source is preferably ammonium formate.

In yet other embodiments in combination with the foregoing, the first aryl compound comprises a first 6-membered carbocyclic ring, the first 6-membered carbocyclic ring having the first and second ring atoms of the first aryl compound. For example, the first aryl compound may comprise a phenyl ring or substituted phenyl ring.

In yet other embodiments in combination with the foregoing, the second aryl compound comprises a second 6-membered carbocyclic ring, the second 6-membered carbocyclic ring comprising the first ring atom of the second aryl compound. For example, the second aryl compound may comprise a phenyl ring or substituted phenyl ring.

In yet other embodiments in combination with the foregoing, the first aryl compound comprises a 5-6-membered heteroaryl ring, the 5-6-membered heteroaryl ring comprising the first and second ring atoms of the first aryl compound and the first ring atom of the first aryl compound is a carbon atom. For example, the first aryl compound may comprise a pyridine, thiophene, or furan ring.

In yet other embodiments in combination with the foregoing, the second aryl compound comprises a 5-6-membered heteroaryl ring, the 5-6-membered heteroaryl ring comprising the first ring atom of the second aryl compound and the first ring atom of the second aryl compound is a carbon atom. For example, the second aryl compound may comprise a pyridine, thiophene, or furan ring.

In certain embodiments, the first aryl compound is

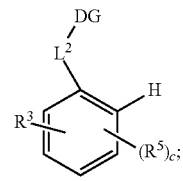

wherein DG is the directing group; $L^2$ is a bond or $L^1$; $L^1$ is a chain comprising 1-5 atoms selected from carbon, nitrogen, oxygen, or sulfur; or $L^1$ is a ring selected from $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^3$ and $R^5$ at each occurrence, are independently hydrogen, $C_{1-6}$alkyl, $C_{2-6}$alkenyl, $C_{2-6}$alknynyl, $C_{1-6}$haloalkyl (e.g. $CFH_2$, $CF_3$ or $CClF_2$), $C_{1-6}$alkoxyalkyl, $C_{1-6}$haloalkoxyalkyl, halogen, cyano, nitro, $OR^{40}$, $COOR^{40}$, $CONR^{41}R^{42}$, $SO_2NR^{41}R^{42}$, $C(O)R^{40}$, $SO_2R^{40}$, $SR^{40}$, $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^{40}$, $R^{41}$, and $R^{42}$ are each independently hydrogen or $C_{1-6}$alkyl; and c is 0 to 3. In a group of compounds according to this embodiment, $L^2$ is a bond and DG is

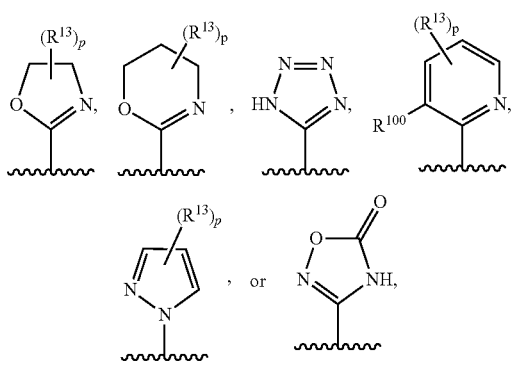

or a salt or protected derivative thereof. In a subgroup of compounds, DG is

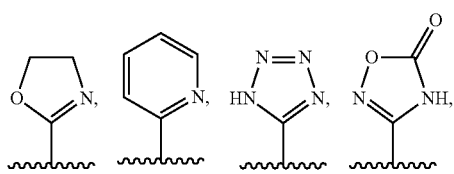

or a salt or protected derivative thereof.

In particular embodiments, the first aryl compound is

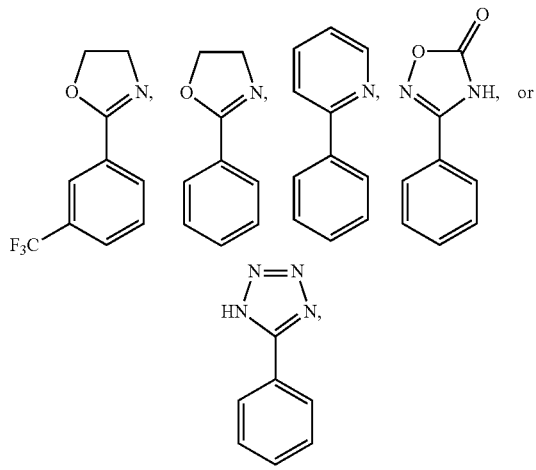

or a salt or protected derivative thereof.

In some embodiments, the second aryl compound is

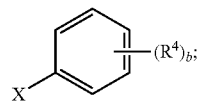

wherein $R^4$, at each occurrence, is independently hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{50}$, $CH_2OPG$, $COOR^{50}$, $CONR^{51}R^{52}$, $SO_2NR^{51}R^{52}$, $C(O)R^{50}$, $SO_2R^{50}$, $SR^{50}$, $C_{3-8}$cycloalkyl, $C_{5-8}$cycloalkenyl, 3-8-membered heterocyclyl, carbocyclic aryl, heteroaryl, spirocyclic heterocyclyl$C_{1-4}$alkyl, carbocyclic aryl$C_{1-4}$alkyl, or heteroaryl$C_{1-4}$alkyl, the $C_{3-8}$cycloalkyl, $C_{5-8}$cycloalkenyl, 3-8-membered heterocyclyl, spirocyclic heterocyclyl, carbocyclic aryl, or heteroaryl being optionally substituted with one or more substituents independently selected from the group consisting of oxo, halogen, $C_{1-6}$alkyl, $C_{1-6}$haloalkyl, $C_{1-6}$alkoxy, $C_{1-6}$haloalkoxy, $OR^{60}$, $CH_2OPG$, CHO, $COOR^{60}$, and cyano; PG, at each occurrence, is independently a protecting group; X is chloro, bromo, or iodo; $R^{50}$, $R^{51}$, and $R^{52}$ are each independently, hydrogen or $C_{1-6}$alkyl; each $R^{60}$ is independently H, $C_{1-6}$alkyl, or 3-8-membered heterocyclyl$C_{1-4}$alkyl, the 3-8-membered heterocyclyl moiety being optionally substituted with $C_{1-6}$alkyl; and b is 0 to 5.

In one group of compounds, the second aryl compound is

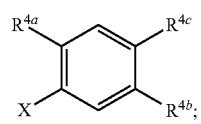

wherein X is chloro, bromo, or iodo; $R^{4a}$ is $C_{1-6}$alkoxy; $R^{4b}$ is $C_{1-6}$alkyl; and $R^{4c}$ is fluoro. In a subgroup of compounds, $R^{4a}$ is methoxy; and $R^{4b}$ is isopropyl.

In another group of compounds, the second aryl compound is

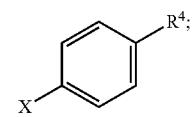

wherein: X is chloro, bromo, or iodo; and $R^4$ is hydrogen, $C_{1-6}$alkyl, $C_{1-6}$haloalkyl, $C_{1-6}$alkoxyalkyl, $CH_2OPG$, $COOR^{50}$, 1,3-diazaspiro[4.4]non-1-en-4-one-3-yl-$CH_2$—, imidazolyl$CH_2$—, or benzimidazolyl$CH_2$—, the 1,3-diazaspiro[4.4]non-1-en-4-one-3-yl being optionally substituted with $C_{1-6}$alkyl, the imidazolyl being optionally substituted with one or more substituents independently selected from the group consisting of $C_{1-6}$alkyl, halogen, $CH_2OPG$, and CHO, and the benzimidazolyl being optionally substituted with one or more substituents independently selected from the group consisting of $OR^{60}$ and $COOR^{60}$; PG, at each occurrence, is independently a protecting group; $R^{50}$ is independently hydrogen or $C_{1-6}$alkyl; and each $R^{60}$ is independently hydrogen, $C_{1-6}$alkyl, or 5-membered heterocyclyl$CH_2$—, the 5-membered heterocyclyl moiety being a 1,3-dioxol-2-one and optionally substituted with $C_{1-6}$alkyl. In a subgroup of compounds, $R^4$ is methyl, $CH_2OPG$, $CH_2$halogen, $COOR^{50}$,

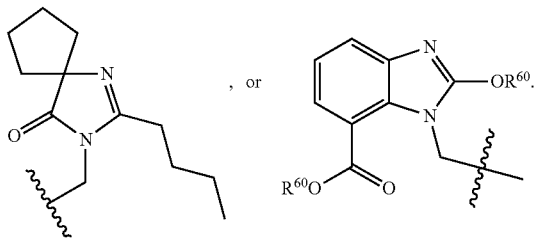

In a further subgroup, each $R^{60}$ is independently $C_{1-6}$alkyl or

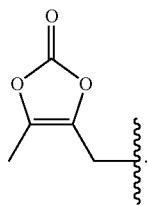 [SMILES: *Cc1oc(=O)oc1C]

In still other embodiments, the second aryl compound is

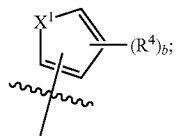

wherein $X^1$ is O or S; $R^4$, at each occurrence, is independently hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{50}$, $CH_2OPG$, $COOR^{50}$, $CONR^{51}R^{52}$, $SO_2NR^{51}R^{52}$, $C(O)R^{50}$, $SO_2R^{50}$, $SR^{50}$, $C_{3-8}$cycloalkyl, $C_{5-8}$cycloalkenyl, 3-8-membered heterocyclyl, carbocyclic aryl, heteroaryl, carbocyclic aryl$C_{1-4}$alkyl, or heteroaryl$C_{1-4}$alkyl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, $OR^{60}$, $COOR^{60}$, and cyano; PG is a protecting group; X is chloro, bromo, or iodo; $R^{50}$, $R^{51}$, $R^{52}$, and $R^{60}$ are each independently hydrogen or $C_{1-6}$alkyl; and b is 0 to 2.

In some embodiments, the biaryl compound produced by the method of the invention is

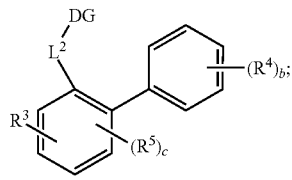

wherein DG is the directing group; $L^2$ is a bond or $L^1$; $L^1$ is a chain comprising 1-5 atoms selected from carbon, nitrogen, oxygen, or sulfur; or $L^1$ is a ring selected from $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^3$ and $R^5$ at each occurrence, are independently, hydrogen, $C_{1-6}$alkyl, $C_{2-6}$alkenyl, $C_{2-6}$alknynyl, $C_{1-6}$haloalkyl (e.g. $CFH_2$, $CF_3$ or $CClF_2$), $C_{1-6}$alkoxyalkyl, $C_{1-6}$haloalkoxyalkyl, halogen, cyano, nitro, $OR^{40}$, $COOR^{40}$, $CONR^{41}R^{42}$, $SO_2NR^{41}R^{42}$, $C(O)R^{40}$, $SO_2R^{40}$, $SR^{40}$, $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^4$, at each occurrence, is independently hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{50}$, $CH_2OPG$, $COOR^{50}$, $CONR^{51}R^{52}$, $SO_2NR^{51}R^{52}$, $C(O)R^{50}$, $SO_2R^{50}$, $SR^{50}$, $C_{3-8}$cycloalkyl, $C_{5-8}$cycloalkenyl, 3-8-membered heterocyclyl, carbocyclic aryl, heteroaryl, spirocyclic heterocyclyl$C_{1-4}$alkyl, carbocyclic aryl$C_{1-4}$alkyl, or heteroaryl$C_{1-4}$alkyl, the $C_{3-8}$cycloalkyl, $C_{5-8}$cycloalkenyl, 3-8-membered heterocyclyl, spirocyclic heterocyclyl, carbocyclic aryl, or heteroaryl being optionally substituted with one or more substituents independently selected from the group consisting of oxo, halogen, $C_{1-6}$alkyl, $C_{1-6}$haloalkyl, $C_{1-6}$alkoxy, $C_{1-6}$haloalkoxy, $OR^{60}$, $COOR^{60}$, $CH_2OPG$, CHO, and cyano; PG, at each occurrence is independently a protecting group; $R^{40}$, $R^{41}$, $R^{42}$, $R^{50}$, $R^{51}$, and $R^{52}$ are each independently hydrogen or $C_{1-6}$alkyl; each $R^{60}$ is independently H, $C_{1-6}$alkyl, or 3-8-membered heterocyclyl$C_{1-4}$alkyl, the 3-8-membered heterocyclyl moiety being optionally substituted with $C_{1-6}$alkyl; b is 0 to 5; and c is 0 to 3.

In certain embodiments, the biaryl compound produced by the method of the invention is

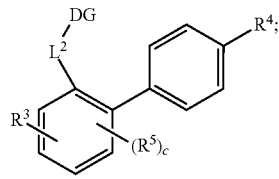

wherein DG, $L^2$, $R^3$, $R^5$, and c are as defined elsewhere herein and $R^4$ is hydrogen, $C_{1-6}$alkyl, $C_{1-6}$haloalkyl, $C_{1-6}$alkoxyalkyl, $CH_2OPG$, $COOR^{50}$, 1,3-diazaspiro[4.4]non-1-en-4-one-3-yl-$CH_2$—, imidazolyl$CH_2$—, or benzimidazolyl$CH_2$—, the 1,3-diazaspiro[4.4]non-1-en-4-one-3-yl being optionally substituted with $C_{1-6}$alkyl, the imidazolyl being optionally substituted with one or more substituents independently selected from the group consisting of $C_{1-6}$alkyl, halogen, $CH_2OPG$, and CHO, and the benzimidazolyl being optionally substituted with one or more substituents independently selected from the group consisting of $OR^{60}$ and $COOR^{60}$; PG, at each occurrence, is independently a protecting group; $R^{50}$ is independently hydrogen or $C_{1-6}$alkyl; and each $R^{60}$ is independently hydrogen, $C_{1-6}$alkyl, or 5-membered heterocyclyl$CH_2$—, the 5-membered heterocyclyl moiety being a 1,3-dioxol-2-one and optionally substituted with $C_{1-6}$alkyl. In a subgroup of compounds, $R^4$ is methyl, $CH_2OPG$, $CH_2$halogen, $COOR^{50}$,

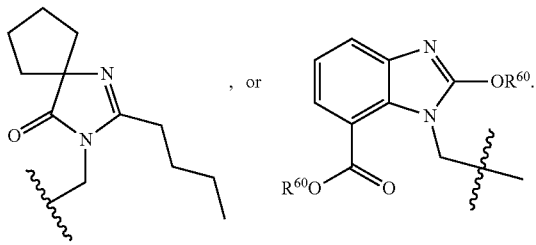, or 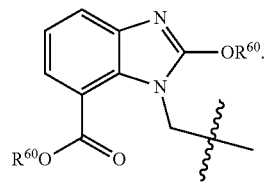

or a salt or protected derivative thereof, and $R^4$ is methyl, $CH_2OPG$, $CH_2$halogen, $COOR^{50}$, or In a further subgroup, each $R^{60}$ is independently $C_{1-6}$alkyl or

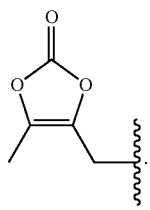 [SMILES: *Cc1oc(=O)oc1C]

In one group of compounds, the biaryl compound is

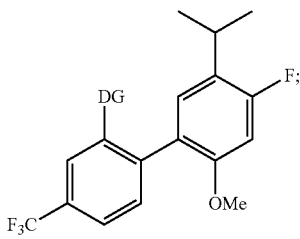

DG is

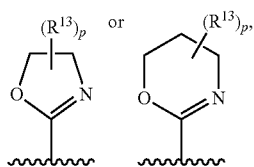

and $R^{13}$ and p are as defined elsewhere herein. In a subgroup, DG is

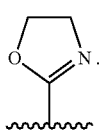

In another group of compounds, the biaryl compound is

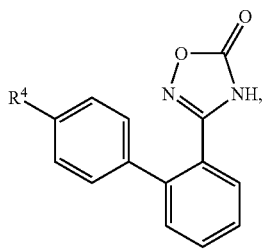

In certain embodiments according to this aspect of the invention, the reaction of the first aryl compound with the second aryl compound may be conducted at a temperature above ambient temperature. For example, the reaction may be conducted at temperatures from about 50 to about 100° C. or at reflux.

In certain embodiments according to this aspect of the invention, the reaction of the first aryl compound with the second aryl compound may be conducted in the presence of a base such as, for example, tertiary amines, pyridines and alkali metal acetates, alkali metal hydroxides, alkali metal alkoxides, alkali metal phosphates, alkali metal carbonates, and alkali metal hydrogen carbonates. More preferably, the base is chosen from NaOAc, KOAc, $K_2CO_3$, $Na_2CO_3$, $CaCO_3$, $K_3PO_4$, $NaHCO_3$, CsOAc, MesCOOK, $C_5H_9KO_2$ (potassium pivalate), $C_5H_9NaO$ (sodium pivalate), or trialkylamines, or mixtures thereof, in which the alkyl groups each preferably contain, independently of each other, 1 to 20, in particular 1 to 10 carbon atoms, for example triethylamine, tri(n-butyl)amine, methyldiisopropylamine or methyldicyclohexylamine. In certain embodiments, the base is potassium carbonate.

In certain embodiments, the reaction may be conducted exposed to the ambient atmosphere (i.e., not under an inert atmosphere).

In certain embodiments, the $[RuCl_2(arene)]_2$ complex is $[RuCl_2(benzene)]_2$, $[RuCl_2(p\text{-cymene})]_2$, $[RuCl_2(hexamethylbenzene)]_2$, $[RuCl_2(biphenyl)]_2$, $[RuCl_2(mesitylene)]_2$, or $[RuCl_2(indane)]_2$. In certain preferred embodiments, the $[RuCl_2(arene)]_2$ complex is $[RuCl_2(p\text{-cymene})]_2$.

In still other embodiments, the reaction of the first aryl compound with the second aryl compound may be conducted in the presence of a co-solvent. For example, the co-solvent includes, but is not limited to, ethanol, methanol, isopropanol, acetone, butanol, methylethylketone, acetonitrile, N-methylpyrrolidinone, or N,N-dimethylformamide, or mixtures thereof.

3.0 Ruthenium Catalysts

In a second aspect of the invention are provided ruthenium catalysts prepared by the reaction of a $[RuCl_2(arene)]_2$ complex with a source of formate. For example, catalysts prepared from $[RuCl_2(arene)]_2$ and a formate source may be prepared by reacting a $[RuCl_2(arene)]_2$ complex with ammonium formate. Alternatively, a $[RuCl_2(arene)]_2$ complex may be reacted with sodium formate to form the ruthenium catalysts of the invention. Other sources of formate include those described elsewhere herein. Likewise, suitable arenes include those described elsewhere herein (e.g., $[RuCl_2(p\text{-cymene})]_2$).

In certain embodiments, the ruthenium catalyst of the invention is prepared from $[RuCl_2(arene)]_2$ and a formate source and used in situ. In other embodiments, the ruthenium catalyst prepared from [RuCl$_2$(arene)]$_2$ and a formate source may be isolated and optionally purified prior to use.

In certain embodiments, the ruthenium catalyst prepared from [RuCl$_2$(arene)]$_2$ and a formate source is formed in situ by reacting 1 part of a [RuCl$_2$(arene)]$_2$ complex with about 5 to about 15 parts of a source of formate. The in situ formation of the ruthenium catalyst may be carried out in aqueous media in the presence of an optional base (e.g., potassium carbonate) and the first and second aryl compounds, and may optionally include the application of heat. Optionally the base (e.g., potassium carbonate) may be added (about 1 to about 3 equivalents). The optional bases include those described elsewhere herein.

In certain embodiments, the ruthenium catalyst prepared from [RuCl$_2$(arene)]$_2$ and a formate source may be prepared and isolated and optionally purified. When separately preparing and isolating the ruthenium catalyst, 1 part of a [RuCl$_2$(arene)]$_2$ may be reacted with about 1 to about 15 parts of a source of formate. In certain embodiments, about 1 part to about 5 parts of the source of formate may be used. In a preferred embodiment, about 4 parts of the source of formate may be used.

When preparing the ruthenium catalyst prepared from [RuCl$_2$(arene)]$_2$ and a formate source for isolation, organic solvents (e.g., dichloromethane) may be used when mixing the reactants and the reaction may be conducted at room temperature. The ruthenium catalyst may be isolated by concentrating the reaction mixture and precipitating/crystallizing the product by the addition of a non-polar solvent (e.g., hexane). The product may be collected, washed with a suitable organic solvent (e.g., diethyl ether) and dried. In certain embodiments, the reaction may be conducted under an ambient atmosphere and/or with the exclusion of moisture. This catalyst may be used to prepare useful aryl-aryl compounds. The isolated catalyst may alleviate the need to use additional amounts of [RuCl$_2$(arene)]$_2$ or formate.

4.0 Compounds Comprising a 1,2,4-oxadiazol-5(4H)-one and Processes for Preparing Biaryls Therefrom In a third aspect of the invention are provided methods of preparing a biaryl compound comprising reacting a first aryl compound with a second aryl compound in the presence of a catalytically effective amount of a [RuCl$_2$(arene)]$_2$ complex; the first aryl compound comprising first and second ring atoms, the second ring atom being appended with a directing group

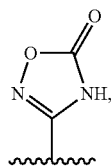

or a salt or protected derivative thereof, and the second ring atom being located ortho to the first ring atom; the second aryl compound comprising a first ring atom, the first ring atom being substituted with a leaving group; wherein the reacting of the first aryl compound with the second aryl compound forms a bond between the first ring atom of the first aryl compound and the first ring atom of the second aryl compound.

It will be understood by one skilled in the art that the DG

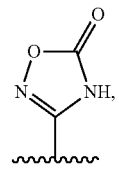

according to each of the aspects of the present invention, may exist in different tautomeric forms:

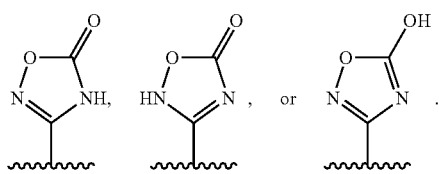 [SMILES: *c1noc(=O)[nH]1 ; *c1nc(=O)o[nH]1 ; *c1noc(O)n1]

In some embodiments, the first aryl compound is

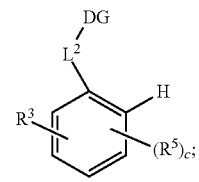

wherein DG is

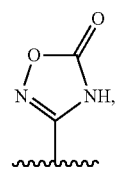

or a salt or protected derivative thereof; L$^2$ is a bond or L$^1$; L$^1$ is a chain comprising 1-5 atoms selected from carbon, nitrogen, oxygen, or sulfur; or L$^1$ is a ring selected from C$_{3-8}$cycloalkyl, C$_{5-8}$cycloalkenyl, 3-8-membered heterocyclyl, carbocyclic aryl, or heteroaryl, the C$_{3-8}$cycloalkyl, C$_{5-8}$cycloalkenyl, 3-8-membered heterocyclyl, carbocyclic aryl, or heteroaryl being optionally substituted with one or more substituents independently selected from the group consisting of halogen, C$_{1-6}$alkyl, C$_{1-6}$haloalkyl, C$_{1-6}$alkoxy, C$_{1-6}$haloalkoxy, and cyano; R$^3$ and R$^5$ at each occurrence, are independently, hydrogen, C$_{1-6}$alkyl, C$_{2-6}$alkenyl, C$_{2-6}$alkynyl, C$_{1-6}$haloalkyl, C$_{1-6}$alkoxyalkyl, C$_{1-6}$haloalkoxyalkyl, halogen, cyano, nitro, OR$^{40}$, COOR$^{40}$, CONR$^{41}$R$^{42}$, SO$_2$NR$^{41}$R$^{42}$, C(O)R$^{40}$, SO$_2$R$^{40}$, SR$^{40}$, C$_{3-8}$cycloalkyl, C$_{5-8}$cycloalkenyl, 3-8-membered heterocyclyl, carbocyclic aryl, or heteroaryl, the C$_{3-8}$cycloalkyl, C$_{5-8}$cycloalkenyl, 3-8-membered heterocyclyl, carbocyclic aryl, or heteroaryl being optionally substituted with one or more substituents independently selected from the group consisting of halogen, C$_{1-6}$alkyl, C$_{1-6}$haloalkyl, C$_{1-6}$alkoxy, C$_{1-6}$haloalkoxy, and cyano; R$^{40}$, R$^{41}$, and R$^{42}$ are each independently, hydrogen or C$_{1-6}$alkyl; and c is 0 to 3.

In other embodiments, the first aryl compound is

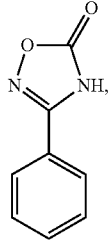

or a salt or protected derivative thereof.

In still other embodiments, the second aryl compound is

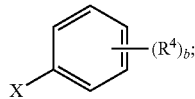

wherein $R^4$, at each occurrence, is independently hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{50}$, $CH_2OPG$, $COOR^{50}$, $CONR^{51}R^{52}$, $SO_2NR^{51}R^{52}$, $C(O)R^{50}$, $SO_2R^{50}$, $SR^{50}$, $C_{3-8}$cycloalkyl, $C_{5-8}$cycloalkenyl, 3-8-membered heterocyclyl, carbocyclic aryl, heteroaryl, carbocyclic aryl$C_{1-4}$alkyl, or heteroaryl$C_{1-4}$alkyl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, $OR^{60}$, $CH_2OPG$, CHO, $COOR^{60}$, and cyano; PG, at each occurrence, is independently a protecting group; X is chloro, bromo, or iodo; $R^{50}$, $R^{51}$, and $R^{52}$ are each independently, hydrogen or $C_{1-6}$alkyl; each $R^{60}$ is independently H, $C_{1-6}$alkyl, or 3-8-membered heterocyclyl$C_{1-4}$alkyl, the 3-8-membered heterocyclyl moiety being optionally substituted with $C_{1-6}$alkyl; and b is 0 to 5.

In yet other embodiments, the second aryl compound is

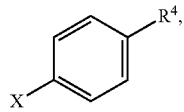

wherein: X is chloro, bromo, or iodo; and $R^4$ is $C_{1-6}$alkyl, $C_{1-6}$haloalkyl, $C_{1-6}$alkoxyalkyl, $CH_2OPG$, $COOR^{50}$, imidazolyl$CH_2$—, or benzimidazolyl$CH_2$—, the imidazolyl being optionally substituted with one or more substituents independently selected from the group consisting of $C_{1-6}$alkyl, halogen, $CH_2OPG$, and CHO, and the benzimidazolyl being optionally substituted with one or more substituents independently selected from the group consisting of $OR^{60}$ and $COOR^{60}$; $R^{50}$ is independently hydrogen or $C_{1-6}$alkyl; and each $R^{60}$ is independently hydrogen, $C_{1-6}$alkyl, or 5-membered heterocyclyl$CH_2$—, the 5-membered heterocyclyl moiety being a 1,3-dioxol-2-one and optionally substituted with $C_{1-6}$alkyl. In one group of compounds, $R^4$ is methyl, $CH_2OPG$, $CH_2$halogen, $COOR^{50}$, or

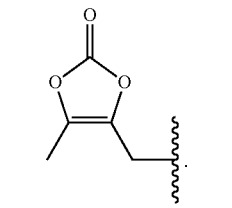 [SMILES: *Cc1oc(=O)oc1C]

In a further subgroup, each $R^{60}$ is independently $C_{1-6}$alkyl or

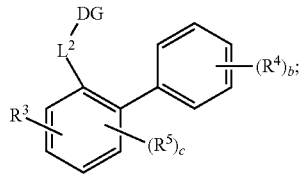

In some embodiments, the biaryl compound is

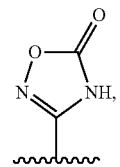

wherein DG is or a salt or protected derivative thereof; $L^2$ is a bond or $L^1$; $L^1$ is a chain comprising 1-5 atoms selected from carbon, nitrogen, oxygen, or sulfur; or $L^1$ is a ring selected from $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^3$ and $R^5$ at each occurrence, are each independently, hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{40}$, $COOR^{40}$, $CONR^{41}R^{42}$, $SO_2NR^{41}R^{42}$, $C(O)R^{40}$, $SO_2R^{40}$, $SR^{40}$, $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^4$, at each occurrence, is independently hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{50}$, $CH_2OPG$, $COOR^{50}$, $CONR^{51}R^{52}$, $SO_2NR^{51}R^{52}$, $C(O)R^{50}$, $SO_2R^{50}$, $SR^{50}$, $C_{3-8}$cycloalkyl, $C_{5-8}$cycloalkenyl, 3-8-membered heterocyclyl, carbocyclic aryl, heteroaryl, or heteroaryl$CH_2$—, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, $OR^{60}$, $COOR^{60}$, $CH_2OPG$, CHO,' and cyano; PG, at each occurrence, is independently a protecting group; $R^{40}$, $R^{41}$, $R^{42}$, $R^{50}$, $R^{51}$, and $R^{52}$ are each independently hydrogen or $C_{1-6}$alkyl; each $R^{60}$ is independently H, $C_{1-6}$alkyl, or 3-8-membered heterocyclyl$C_{1-4}$alkyl, the 3-8-membered heterocyclyl moiety being optionally substituted with $C_{1-6}$alkyl; b is 0 to 5; and c is 0 to 3.

In certain embodiments, the biaryl compound produced by the method of the invention is

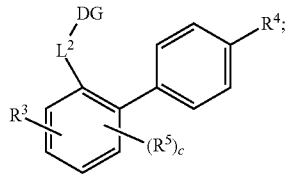

wherein $L^2$, $R^3$, $R^5$, and c are as defined elsewhere herein; DG is

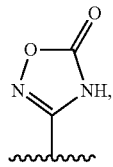

or a salt or protected derivative thereof; and $R^4$ is hydrogen, $C_{1-6}$alkyl, $C_{1-6}$haloalkyl, $C_{1-6}$alkoxyalkyl, $CH_2OPG$, $COOR^{50}$, imidazolyl$CH_2$—, or benzimidazolyl$CH_2$—, the imidazolyl being optionally substituted with one or more substituents independently selected from the group consisting of $C_{1-6}$alkyl, halogen, $CH_2OPG$, and CHO, and the benzimidazolyl being optionally substituted with one or more substituents independently selected from the group consisting of $OR^{60}$ and $COOR^{60}$; PG, at each occurrence, is independently a protecting group; $R^{50}$ is independently hydrogen or $C_{1-6}$alkyl; and each $R^{60}$ is independently hydrogen, $C_{1-6}$alkyl, or 5-membered heterocyclyl$CH_2$—, the 5-membered heterocyclyl moiety being a 1,3-dioxol-2-one and optionally substituted with $C_{1-6}$alkyl. In a subgroup of compounds, $R^4$ is methyl, $CH_2OPG$, $CH_2$halogen, $COOR^{50}$, or

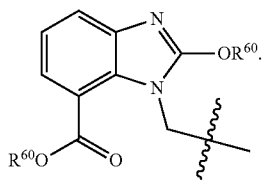

In a further subgroup, each $R^{60}$ is independently $C_{1-6}$alkyl or

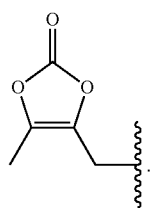 [SMILES: *Cc1oc(=O)oc1C]

In certain embodiments, the biaryl compound is

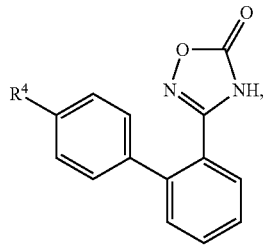

or a salt or protected derivative thereof; and $R^4$ is methyl, $CH_2OPG$, $CH_2$halogen, $COOR^{50}$, or

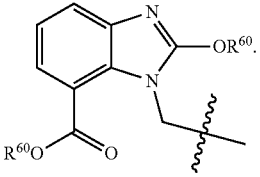

In a subgroup, each $R^{60}$ is independently $C_{1-6}$alkyl or

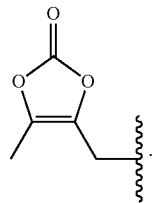 [SMILES: *Cc1oc(=O)oc1C]

In other embodiments according to the third aspect are biaryl compounds of the invention of formula

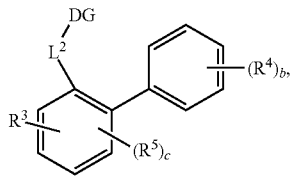

or salt thereof, wherein; DG is

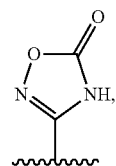

or a salt or protected derivative thereof; $L^2$ is a bond or $L^1$; $L^1$ is a chain comprising 1-5 atoms selected from carbon, nitrogen, oxygen, or sulfur; or $L^1$ is a ring selected from $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^3$ and $R^5$ at each occurrence, are each independently, hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{40}$, $COOR^{40}$, $CONR^{41}R^{42}$, $SO_2NR^{41}R^{42}$, $C(O)R^{40}$, $SO_2R^{40}$, $SR^{40}$, $C_{3-8}$cycloalkyl, $C_{5-8}$cycloalkenyl, 3-8-membered heterocyclyl, carbocyclic aryl, or heteroaryl, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, and cyano; $R^4$, at each occurrence, is independently hydrogen, $C_{1-6}$alkyl, $C_{2-6}$alkenyl, $C_{2-6}$alknynyl, $C_{1-6}$haloalkyl, $C_{1-6}$alkoxyalkyl, $C_{1-6}$haloalkoxyalkyl, halogen, cyano, nitro, $OR^{50}$, $CH_2OPG$, $COOR^{50}$, $CONR^{51}R^{52}$, $SO_2NR^{51}R^{52}$, $C(O)R^{50}$, $SO_2R^{50}$, $SR^{50}$, $C_{3-8}$cycloalkyl, $C_{5-8}$cycloalkenyl, 3-8-membered heterocyclyl, carbocyclic aryl, heteroaryl, or heteroaryl$CH_2$—, the $C_{3-8}$cycloalkyl, $C_{5-8}$cycloalkenyl, 3-8-membered heterocyclyl, carbocyclic aryl, or heteroaryl being optionally substituted with one or more substituents independently selected from the group consisting of halogen, $C_{1-6}$alkyl, $C_{1-6}$haloalkyl, $C_{1-6}$alkoxy, $C_{1-6}$haloalkoxy, $OR^{60}$, $CH_2OPG$, CHO,' and cyano; PG, at each occurrence, is independently a protecting group; $R^{40}$, $R^{41}$, $R^{42}$, $R^{50}$, $R^{51}$, $R^{52}$, and $R^{60}$ are each independently hydrogen or $C_{1-6}$alkyl; b is 0 to 5; and c is 0 to 3. In one group of compounds a biaryl compound of the invention is

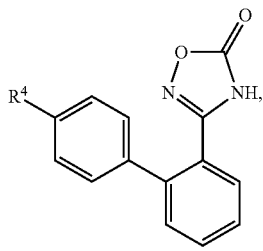

or a salt or optionally protected derivative thereof; and $R^4$ is methyl, $CH_2OPG$, $CH_2$halogen, or $COOR^{50}$.

The group

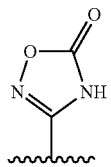

may be substituted with a suitable protecting group such as, for example, a benzyl protecting group. Suitable benzyl protecting groups may include without limitation benzyl, 4-methoxybenzyl, 3,4-dimethoxybenzyl, etc.

In certain embodiments, the methods according to this aspect of the invention may be conducted in an organic solvent. In certain embodiment, the organic solvent is N-methylpyrrolidinone, N,N-dimethylformamide, or N,N-dimethylacetamide, or mixtures thereof.

In other embodiments, the methods according to this aspect of the invention may be conducted in the presence of a source of formate, including those described hereinabove.

In other embodiment, the methods according to this aspect of the invention may be conducted in the presence of a base, such as those described hereinabove.

5.0 Preparation and Use of Biaryl Compounds

Biaryl compounds III may be prepared according to the process depicted in Scheme 1, wherein $R^3$, $R^4$, $R^5$, $L^2$, DG, X, b, and c are as defined herein.

Scheme 1

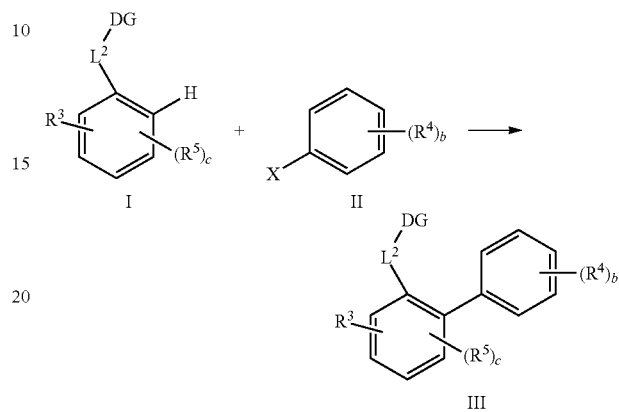

The process of Scheme 1 may be carried out by reacting formula I (1 equivalent) with formula II (about 1 to about 4 equivalents), in the presence of a catalytically effective amount (e.g., about 0.01 to about 0.3 equivalents) of [$RuCl_2$(arene)]$_2$ complex (e.g., [$RuCl_2$(p-cymene)]$_2$) and a source of formate (about 1 to about 2 equivalents) in water. Optionally a base (e.g., potassium carbonate) may be added (about 1 to about 3 equivalents). The reaction may be heated up to about reflux and may be conducted under an insert atmosphere or exposed to the ambient atmosphere. The concentration of formula I may be about 0.1 M to about 1 M, although other concentrations may also be used, depending on the particular reaction.

Examples of suitable bases are mentioned in for example "Metal-catalyzed Cross-coupling reactions", F. Diederich and P. J. Stang Eds., Wiley-VCH, Weinheim, 1998, Chapters 2 and 3. The base is preferably chosen from the group of tertiary amines, pyridines and alkali metal acetates, alkali metal hydroxides, alkali metal alkoxides, alkali metal phosphates, alkali metal carbonates, and alkali metal hydrogen carbonates. More preferably, the base is chosen from NaOAc, KOAc, $K_2CO_3$, $Na_2CO_3$, $CaCO_3$, $K_3PO_4$, $NaHCO_3$, CsOAc, MesCOOK, $C_5H_9KO_2$ (potassium pivalate), $C_5H_9NaO$ (sodium pivalate), or trialkylamines, in which the alkyl groups each preferably contain, independently of each other, 1 to 20, in particular 1 to 10 carbon atoms, for example triethylamine, tri(n-butyl)amine, methyldiisopropylamine or methyldicyclohexylamine.

The reaction depicted in Scheme 1 may also be conducted by preparing a ruthenium catalyst formed from [$RuCl_2$(arene)]$_2$ complex and a source of formate separately and adding a catalytically effective amount of the isolated ruthenium catalyst product to the reaction mixture rather than forming the ruthenium catalyst product in situ.

The process depicted in Scheme 1 is merely exemplary. Biaryl compounds where either the first aryl compound and/or the second aryl compound is a heteroaryl may be prepared using the illustrated process.

Biaryl compounds produced using the processes of the invention may be useful as intermediates in the synthesis of biologically active biaryl-containing molecules.

Depicted in Scheme 2 is a synthetic sequence through which the biaryl compound 1, produced using the processes of the invention, may be converted to compound 5, anacetripib. Anacetripib is an inhibitor of cholesterol ester transfer protein (CETP), which is a plasma glycoprotein that transfers cholesterol ester (CE) from HDL to LDL and VLDL, thereby lowering antiatherogenic HDL and increasing proatherogenic LDL and VLDL.

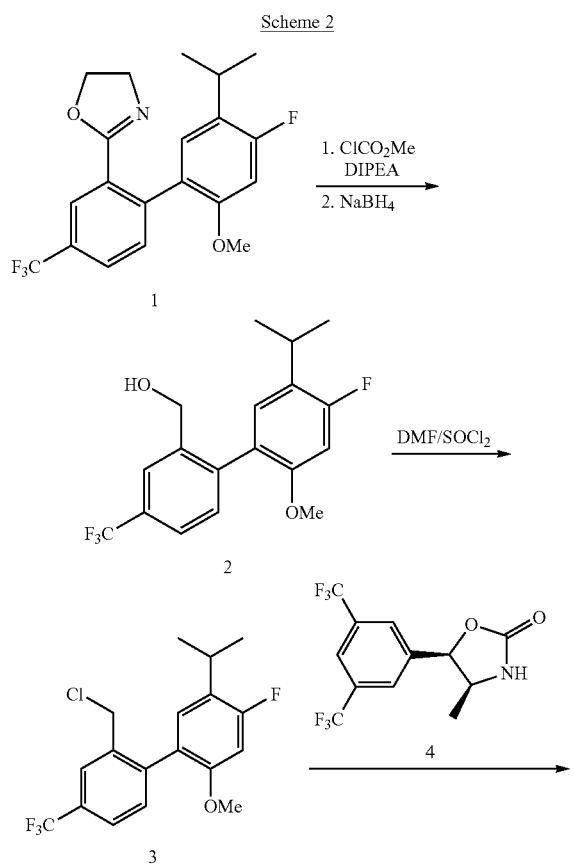

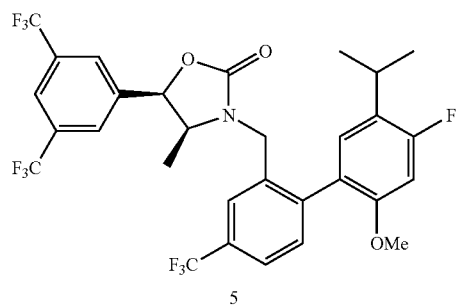

Depicted in Scheme 3 is a synthetic sequence through which the biaryl compound 6, which may be produced from 4-bromotoluene and compound 11 using the processes of the invention, may be converted to compound 9, azilsartan medoxomil. Edarbi (azilsartan medoxomil), a prodrug, is hydrolyzed to azilsartan in the gastrointestinal tract during absorption. Azilsartan is a selective AT1 subtype angiotensin II receptor antagonist. In Scheme 3, the methyl group in 6 may be functionalized such as by benzylic bromination or oxidation to a corresponding benzyl bromide or alcohol. Alternatively, the methyl may be oxidized to the acid and then reduced to the alcohol using known techniques. As a further alternative, a compound 10 may be coupled with 11 using the methods of the invention to produce 7. In compound 10, $Y^1$ may be a protected oxygen (e.g., O-benzyl, O-TBDMS, OMOM, etc.). In compound 7, when $Y^2$ is a protected oxygen, the protecting group may be removed using standard conditions in order to form the corresponding alcohol. And when $Y^2$ is an alcohol, the alcohol may be converted to a suitable leaving group (e.g., OTs) for further reaction to 8.

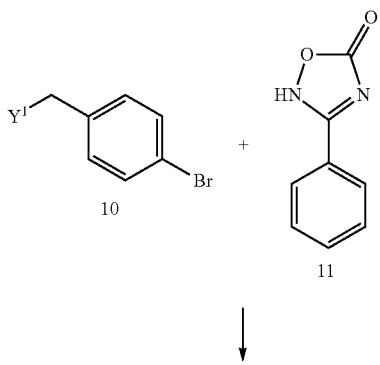

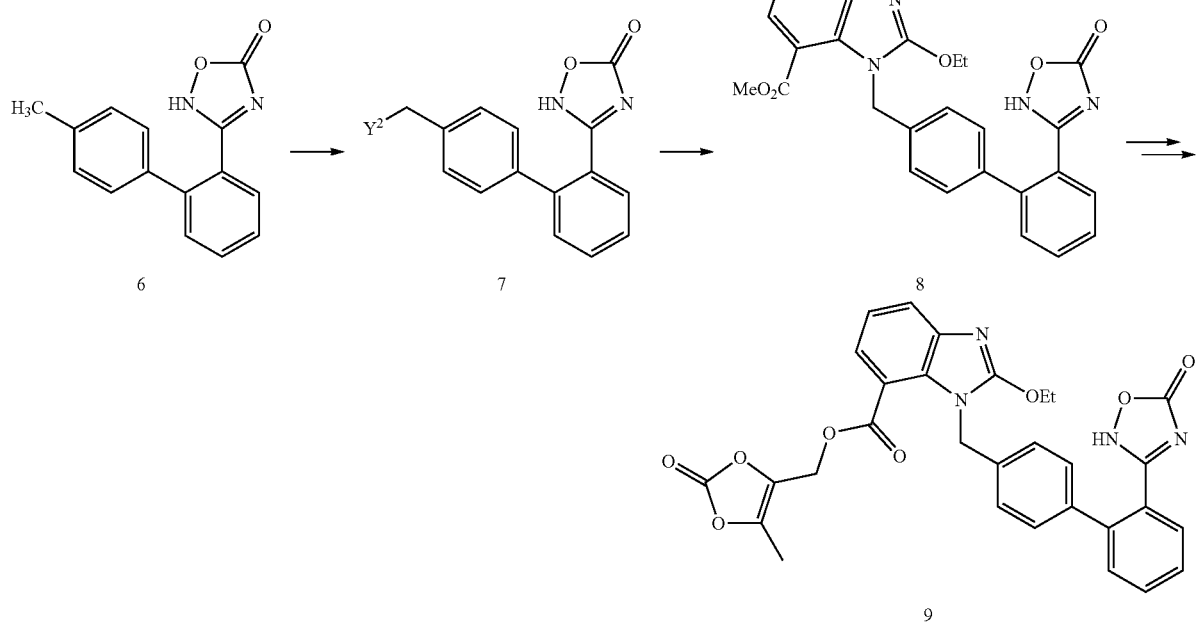

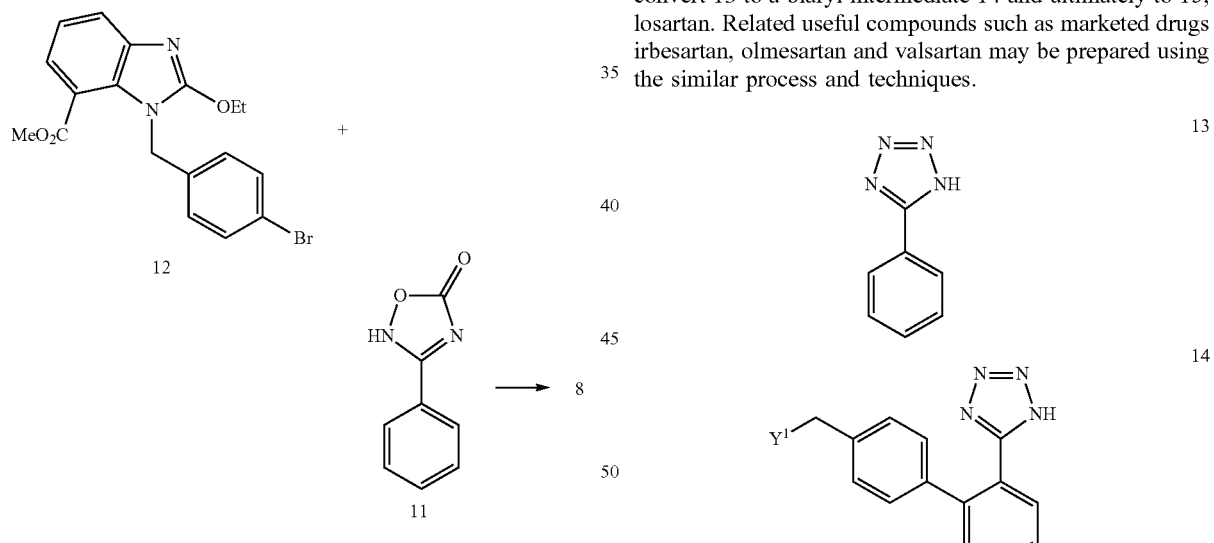

Depicted in Scheme 4 is a further alternative process where 11 may be reacted with 12 to directly produce 8.

may be substituted with a protecting group as described elsewhere herein.

Similar processes and techniques may be employed to convert 13 to a biaryl intermediate 14 and ultimately to 15, losartan. Related useful compounds such as marketed drugs irbesartan, olmesartan and valsartan may be prepared using the similar process and techniques.

It will be understood by one skilled in the art that additional protecting groups may be required to efficiently carry out certain transformations in Schemes 3 and 4. It is within the level of ordinary skill to be able to select such protecting groups. For example, the moiety

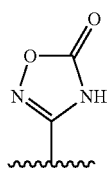

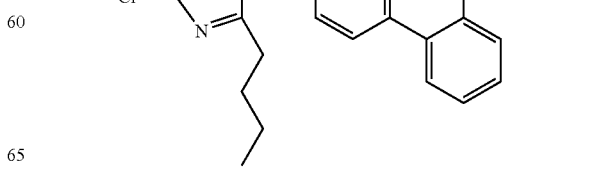

Alternatively the following intermediates may be used for the condensation and later the cyano group may be converted to a tetrazole moiety for preparation of these drugs:

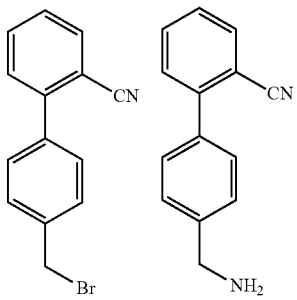

Alternatively, simple aryl tetrazole (appropriately protected with groups such a trityl) and cyano compounds, as illustrated below, may also be condensed with bromo intermediates such as 3-(4-bromobenzyl)-2-butyl-1,3-diazaspiro[4.4]non-1-en-4-one (below), in the synthesis of one such drug example—irbesartan (2-butyl-3-{[2'-(1H-tetrazol-5-yl)biphenyl-4-yl]methyl}-1,3-diazaspiro[4.4]non-1-en-4-one) (see below):

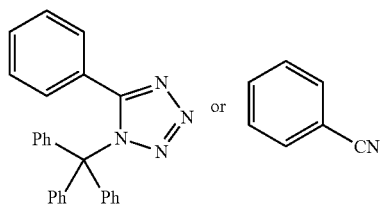 [SMILES: c1ccc(-c2nnnn2C(c2ccccc2)(c2ccccc2)c2ccccc2)cc1 ; N#Cc1ccccc1]

The above two intermediates may be condensed with the following intermediate 3-(4-bromobenzyl)-2-butyl-1,3-diazaspiro[4.4]non-1-en-4-one:

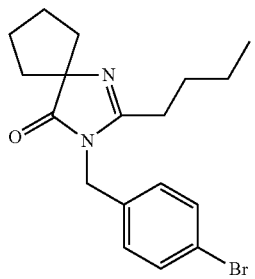 [SMILES: CCCCC1=NC2(CCCC2)C(=O)N1Cc1ccc(Br)cc1]

to prepare a biaryl compound, which may subsequently be converted to irbesartan.

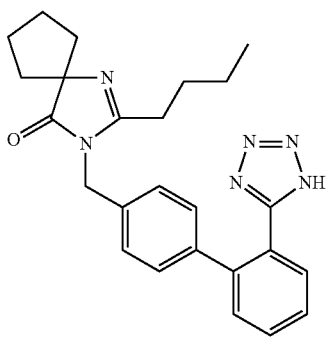

Irbesartan

6.0 Examples

6.1 C—H Insertion and Coupling with In-Situ Generated Ruthenium Catalyst from [RuCl$_2$(p-cymene)]$_2$ and a Source of Formate

Example 1

A mixture of 2-(3-(trifluoromethyl)phenyl)-4,5-dihydrooxazole (88 mg, 0.41 mmol), bromobenzene (242 mg, 1.54 mmol), sodium formate (50 mg, 0.73 mmol), K$_2$CO$_3$ (205 mg, 1.48 mmol), and [RuCl$_2$(p-cymene)]$_2$ (44 mg, 0.072 mmol) was vacuumed and purged with argon three times. A sample of freshly distilled H$_2$O (2 mL) that was vacuumed and purged with argon was added to the reaction mixture. After final vacuum and argon purge, the heterogeneous mixture was allowed to heat at reflux (oil bath temperature: 110° C.). After 18 h, TLC showed quantitative conversion. The dark black reaction mixture was cooled down to room temperature and passed through a small Celite column (50 g). The celite was washed with additional EtOAc (10 mL). The Filtrate was concentrated under reduced pressure to a crude mixture which was purified by gradient SiO$_2$ column chromatography (5-20% EtOAc/hex) to give isolated yield of 60 mg product 2-(4-(trifluoromethyl)-[1,1'-biphenyl]-2-yl)-4,5-dihydrooxazole. $^1$H NMR (500 MHz, CDCl3) δ 3.9 (m, 2H), 4.2 (m, 2H), 7.3-7.7 (m, 5H), 7.51 (d, 1H), 7.77 (m, 1H), 8.1 (m, 1H); LRMS (EI) m/z 292.

Example 2

A mixture of 2-(3-(trifluoromethyl)phenyl)-4,5-dihydrooxazole (41 mg, 0.19 mmol), 1-bromo-4-fluoro-5-isopropyl-2-methoxybenzene (47 mg, 0.19 mmol), sodium formate (20 mg, 0.29 mmol), K$_2$CO$_3$ (90 mg, 0.65 mmol), and [RuCl$_2$(p-cymene)]$_2$ (28 mg, 0.045 mmol) was vacuumed and purged with argon three times. A sample of freshly distilled H$_2$O (2 mL) that was vacuumed and purged with argon was added to the reaction mixture. After final vacuum and argon purge, the heterogeneous mixture was allowed to heat at reflux (oil bath temperature: 110° C.). After 16 h, TLC monitoring showed quantitative conversion. The dark black reaction mixture was cooled down to room temperature and passed through a small Celite column (50 g). The celite was washed with additional EtOAc (75 mL). The Filtrate was concentrated under reduced pressure to a crude mixture which was purified by gradient SiO$_2$ column chromatography (5-20% EtOAc/hex) to afford isolated yield of 32 mg of the product 2-(4'-fluoro-5'-isopropyl-2'-methoxy-4-(trifluoromethyl)-[1,1'-biphenyl]-2-yl)-4,5-dihydrooxazole. $^1$H NMR (500 MHz, CDCl3) δ 1.24 (d, 6H), 3.2 (m, 1H), 3.7 (s, 3H), 3.9 (dd, 2H), 4.15 (dd, 2H), 6.6 (d, 1H), 7.15 (d, 1H), 7.49 (d, 1H), 7.73 (d, 1H), 8.13 (s, 1H); HRMS (EI) calc 382.14188, obtained 382.14301.

Example 3

A mixture of 2-(3-(trifluoromethyl)phenyl)-4,5-dihydrooxazole (41 mg, 0.19 mmol), 1-bromo-4-fluoro-5-isopropyl-2-methoxybenzene (47 mg, 0.19 mmol), NH$_4$HCO$_2$ (20 mg, 0.32 mmol), K$_2$CO$_3$ (90 mg, 0.65 mmol), and [RuCl$_2$(p-cymene)]$_2$ (30 mg, 0.049 mmol) was vacuumed and purged with argon three times. A sample f freshly distilled H$_2$O (2 mL) that was vacuumed and purged with argon was added to the reaction mixture. After final vacuum and argon purge, the heterogeneous mixture was allowed to heat at reflux (oil bath temperature: 110° C.). After 16 h, TLC showed quantitative conversion. The dark black reaction mixture was cooled down to room temperature and passed through a small Celite column (50 g). The celite was washed with additional EtOAc (75 mL). The Filtrate was concentrated under reduced pressure to a crude mixture which was purified by gradient $SiO_2$ column chromatography (5-20% EtOAc/hex) to afford isolated yield of 43 mg of the product 2-(4'-fluoro-5'-isopropyl-2'-methoxy-4-(trifluoromethyl)-[1,1'-biphenyl]-2-yl)-4,5-dihydrooxazole. $^1$H NMR (500 MHz, CDCl3) δ 1.24 (d, 6H), 3.2 (m, 1H), 3.7 (s, 3H), 3.9 (dd, 2H), 4.15 (dd, 2H), 6.6 (d, 1H), 7.15 (d, 1H), 7.49 (d, 1H), 7.73 (d, 1H), 8.13 (s, 1H).

Example 4

A mixture of benzo[h]quinoline (115 mg, 0.64 mmol), bromobenzene (241 mg, 1.53 mmol), $NH_4HCO_2$ (35 mg, 0.55 mmol), $K_2CO_3$ (202 mg, 1.46 mmol), and [RuCl$_2$(p-cymene)]$_2$ (40 mg, 0.065 mmol) was vacuumed and purged with argon three times. A sample of freshly distilled $H_2O$ (2 mL) that was vacuumed and purged with argon was added to the reaction mixture. After final vacuum and argon purge, the heterogeneous mixture was allowed to heat at reflux (oil bath temperature: ~110° C. for 18 hours). The dark black reaction mixture was cooled down to room temperature and passed through a small Celite column (50 g). The celite was washed with additional EtOAc (40 mL). The Filtrate was concentrated under reduced pressure to a crude mixture which was purified by gradient $SiO_2$ column chromatography (5-15% EtOAc/hex) to afford 87 mg of the product 10-phenylbenzo[h]quinolone. $^1$H NMR (500 MHz, CDCl3) δ 7.38 (dd, 1H), 7.40 (m, 5H), 7.55 (dd, 1H), 7.68 (d, 1H), 7.70-7.82 (dd, 2H), 7.93 (dd, 1H), 8.10 (dd, 1H), 8.42 (dd, 1H); HRMS (EI) calc 254.09697, obtained 254.09666.

Example 5

2-Phenylpyridine (178 mg, 1.14 mmol), 4-bromotoluene (412 mg, 2.408 mmol), HCOONH$_4$ (75 mg, 1.20 mmol), $K_2CO_3$ (160 mg, 1.2 mmol), and [RuCl$_2$(p-cymene)]$_2$ (55 mg, 0.089 mmol) in a 25 mL RBF were mixed with deionized $H_2O$ (2 mL). After mixing the heterogeneous mixture was allowed to heat at reflux (oil bath temperature: 110° C.) for 13 hours. The TLC analysis indicated ~90% conversion as a mixture of mono and diarylated phenyl pyridine. No inert atmosphere was necessary—all manipulations were done without seal tubes or pressure reactors.

6.2 C—H Insertion and Coupling without Base

Example 6

A mixture of 2-(3-(trifluoromethyl)phenyl)-4,5-dihydrooxazole (100 mg, 0.46 mmol), bromobenzene (250 mg, 1.59 mmol), NaHCO$_2$ (52 mg, 0.76 mmol) and [RuCl$_2$(p-cymene)]$_2$ (50 mg, 0.081 mmol) was vacuumed and purged with argon for 10 minutes. A sample of freshly distilled $H_2O$ (2 mL) that was vacuumed and purged with argon was added to the reaction mixture. After final vacuum and argon purge, the heterogeneous mixture was allowed to heat at reflux (oil bath temperature: 100° C.-105° C.). After 18 h, the dark black reaction mixture showed ~90% conversion.

Example 7

A 25 mL round bottom flask was degassed by removing air and purging with argon for 5 minutes. A mixture of benzo[h]quinoline (130 mg, 0.72 mmol), bromobenzene (241 mg, 1.53 mmol), HCOONH$_4$ (50 mg, 0.79 mmol), and [RuCl$_2$(p-cymene)]$_2$ (45 mg, 0.07 mmol) were added. A sample of freshly distilled $H_2O$ (2 mL) that was vacuumed and purged with argon was added to the reaction mixture. After final vacuum and argon purge, the heterogeneous mixture was allowed to heat at reflux (oil bath temperature: 100° C.) for 22 hours. TLC revealed that a spot corresponding to desired product previously established was formed about 50% based on analysis.

6.3 Isolated Ruthenium Catalyst from [RuCl$_2$(p-cymene)]$_2$ and Formate

Example 8

RuCl$_2$ (p-cymene) dimer (100 mg, 0.1634 mmol) and ammonium formate (47 mg, 0.6863, 4 equivalents) were mixed in anhydrous dichloromethane (10 mL). The resulting mixture was allowed to stir at room temperature at overnight (~16 hrs). The reaction mixture was then concentrated under reduced pressure to ~5 mL and then hexane was added. The precipitate was filtered and washed with ether, dried (reduced pressure) to afford the product. The reaction was done under normal reflux and no inert atmosphere was created.

Example 9

RuCl$_2$ (p-cymene) dimer (100 mg, 0.1634 mmol) and sodium formate (47 mg, 0.6863, 4 equivalent) were mixed in a round bottom flask with anhydrous dichloromethane (10 mL). The resulting mixture was allowed to stir at room temperature overnight (~20 hrs). The resulting red solution was concentrated to approximately half the volume and then hexanes were slowly added. The mixture was cooled in ice bath to maximize precipitation. The solids were filtered, washed with ethyl acetate (~5 mL), dried via concentration under reduced pressure to afford 115 mg of this product. The reaction was done under normal reflux and no inert atmosphere was created. This product was used as such for coupling step (example 10) without further purification.

Example 10

A mixture of 2 phenylpyridine (134 mg, 0.86 mmol), 4-bromotoluene (530 mg, 3 mmol), the ruthenium catalyst product of Example-9 (54 mg) and $K_2CO_3$ (230 mg, 1.66 mmol) in water (distilled) was heated at reflux. The oil bath was maintained between 110° C.-120° C. The next day TLC analysis with co-TLC of expected products indicated ~95% conversion and the starting material (phenyl pyridine) was present as a light spot.

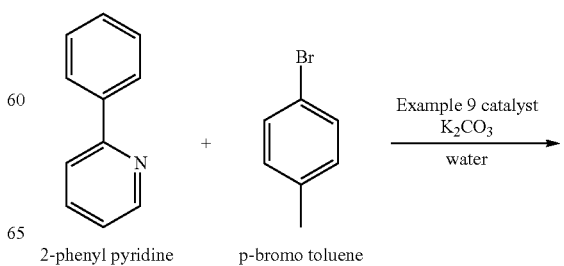

2-phenyl pyridine    p-bromo toluene

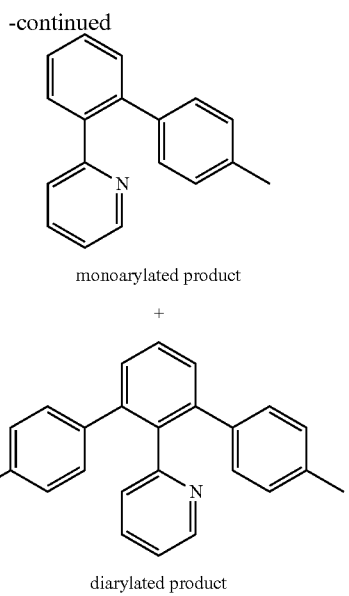

monoarylated product

+ diarylated product

The dark black reaction mixture was worked up by adding 25 mL of ethyl acetate and 12 mL of water and shaking in a separating funnel to ensure maximum extraction. The ethyl acetate layer was further washed with deionized water. 10 mL of the ethyl acetate layer was passed through a small plug of silica (120 mg) to remove solid particles and washed further with ethyl acetate. No attempt was made to separate the mixture of mono and diarylated products and this sample was subjected to GCMS and NMR analysis as such. Based on NMR of the crude product, the ratio of mono- versus di-arylated product was established to be 1.3:0.70. GCT premier was used to record GC MS. Analysis: retention time and retention index on Total Ion Chromatogram (TIC) confirmed that the product was a mixture of di and mono product with minor amounts of staring material (phenyl pyridine). Peak at 13.27 minutes corresponded to the di-arylated product (mass 334.2) while a peak at 9.73 minutes corresponded to the mono-arylated product (244.1). An authentic sample of phenyl pyridine and arylated products was used to confirm the identity of both phenyl pyridine and mono and di arylated products. The remainder of the ethyl acetate layer was passed through small amounts of celite and washed with water or filtered directly through a filter paper; crude yield from all fractions was 171 mg.

The ruthenium catalyst of Example 9 used in Example 10 had been prepared 30 days earlier and kept at room temperature (no inert atmosphere). The reaction was done under normal reflux and there was no need to create an inert atmosphere indicating the stability of the complex of Example 9. This result demonstrates an advantage of the isolated ruthenium catalyst of the invention in terms of storage stability and potential use without special handling conditions (i.e., inert atmosphere).

It will be apparent, however, to one skilled in the art that there several different ways to work up the experiments based on the need and requirements.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. Furthermore, the advantages described above are not necessarily the only advantages of the discovery, and it is not necessarily expected that all of the described advantages will be achieved with every embodiment of the discovery.

What is claimed is:

1. A ruthenium catalyst prepared by
   reacting one part of $[RuCl_2(p\text{-cymene})]_2$ with our parts of sodium formate in dichloromethane to produce a ruthenium catalyst product;
   precipitating or crystallizing the ruthenium catalyst product with hexanes; and
   washing the ruthenium catalyst product with ethyl acetate.

2. The ruthenium catalyst of claim 1, wherein the ruthenium catalyst product is capable of catalyzing the process of preparing a biaryl compound from first and second aryl compounds.

* * * * *

UNITED STATES PATENT AND TRADEMARK OFFICE
CERTIFICATE OF CORRECTION

PATENT NO. : 10,300,471 B2
APPLICATION NO. : 15/028276
DATED : May 28, 2019
INVENTOR(S) : Ali Aiden Koohang and Anita Mehta Page 1 of 1

It is certified that error appears in the above-identified patent and that said Letters Patent is hereby corrected as shown below:

In the Claims

In Column 38, Claim 3, Line 33, delete "our" and insert -- four --.

Signed and Sealed this
Sixteenth Day of July, 2019

Andrei Iancu
*Director of the United States Patent and Trademark Office*